(12) United States Patent
Chua et al.

(10) Patent No.: US 11,020,199 B2
(45) Date of Patent: Jun. 1, 2021

(54) SURGICAL DRAPE

(71) Applicant: Medline Industries, Inc., Mundelein, IL (US)

(72) Inventors: Mark Spencer Chua, Northbrook, IL (US); Michael Seefeldt, Chicago, IL (US)

(73) Assignee: Medline Industries, Inc., Northfield, IL (US)

(*) Notice: Subject to any disclaimer, the term of this patent is extended or adjusted under 35 U.S.C. 154(b) by 422 days.

(21) Appl. No.: 15/069,380

(22) Filed: Mar. 14, 2016

(65) Prior Publication Data
US 2017/0258543 A1     Sep. 14, 2017

(51) Int. Cl.
*A61B 46/00*     (2016.01)
*A61B 46/20*     (2016.01)
(Continued)

(52) U.S. Cl.
CPC .............. *A61B 46/20* (2016.02); *A61B 46/30* (2016.02); *A61B 46/40* (2016.02);
(Continued)

(58) Field of Classification Search
CPC ... A61B 46/00–40; A61B 46/20; A61B 46/30; A61B 46/40; A61B 2046/201;
(Continued)

(56) References Cited

U.S. PATENT DOCUMENTS 3,667,458 A    6/1972   Krebs
3,698,395 A    10/1972   Hasson
(Continued)

FOREIGN PATENT DOCUMENTS

CN    201602900 U    10/2010
CN    201602902      10/2010
(Continued)

OTHER PUBLICATIONS

Australian Patent Application No. 2012223335; Patent Examination Report No. 1; dated Aug. 14, 2015; 4 pages.
(Continued)

*Primary Examiner* — Rachael E Bredefeld
*Assistant Examiner* — Brant T Bennett
(74) *Attorney, Agent, or Firm* — Fitch, Even, Tabin & Flannery LLP

(57) ABSTRACT

Disclosed is a surgical drape configured to selectively allow or block a patient's view of the surgical field, as is desired in Caesarean section operations. Generally, the drape includes a main sheet, a substantially transparent sheet attached to the main sheet proximal the patient's head, and a substantially opaque screen attached to the patient-facing side of the substantially transparent sheet. This substantially opaque screen occludes the patient's visual access through the substantially transparent sheet but may be at least partially removed to permit the patient viewing access through the substantially transparent sheet towards the area of the surgery, without compromising the sterility of the surgical field. Desirably, the drape is provided with an adhesive strip disposed on the sheet or screen to permit reconnection to thereby again occlude the patient's view through the sheet.

16 Claims, 7 Drawing Sheets

(51) Int. Cl.
    *A61B 17/00* (2006.01)
    *A61B 46/23* (2016.01)
(52) U.S. Cl.
    CPC .............. *A61B 2017/00902* (2013.01); *A61B 2046/205* (2016.02); *A61B 2046/236* (2016.02)
(58) Field of Classification Search
    CPC .... A61B 2046/205; A61B 2017/00902; A61B 46/10; A61B 46/23; A61B 2046/236; A61F 2013/00182; A61F 2013/15073; A61G 13/10
    USPC .................................................. 128/849–856
    See application file for complete search history.

(56) References Cited

U.S. PATENT DOCUMENTS

| | | |
|---|---|---|
| 3,707,964 A | 1/1973 | Patience |
| 3,721,242 A | 3/1973 | Krusko |
| 3,750,664 A | 8/1973 | Collins |
| 3,763,857 A | 10/1973 | Schrading |
| 3,791,381 A | 2/1974 | Krzewinski |
| 3,799,161 A | 3/1974 | Collins |
| 3,826,253 A | 7/1974 | Larsh |
| 4,089,331 A | 5/1978 | Hartigan |
| 4,169,472 A | 10/1979 | Morris |
| 4,192,312 A | 3/1980 | Wilson |
| 4,205,668 A | 6/1980 | Criddle |
| D256,161 S | 7/1980 | Oliver |
| 4,384,573 A * | 5/1983 | Elliott ............... A61B 46/00 128/853 |
| 4,471,769 A * | 9/1984 | Lockhart ............ A61B 46/30 128/849 |
| 4,489,720 A | 12/1984 | Morris |
| 4,559,937 A | 12/1985 | Vinson |
| 4,586,498 A | 5/1986 | Morris |
| 4,616,642 A | 10/1986 | Martin |
| 4,798,201 A | 1/1989 | Rawlings |
| 4,869,271 A | 9/1989 | Idris |
| 4,890,628 A | 1/1990 | Jackson |
| 4,899,762 A | 2/1990 | Muller |
| 4,944,737 A | 7/1990 | Bloom |
| 5,042,507 A | 8/1991 | Dowdy |
| 5,060,662 A | 10/1991 | Farnswoth, III |
| 5,195,893 A | 3/1993 | Casale |
| 5,197,493 A | 3/1993 | Grier-Idris |
| 5,209,243 A | 5/1993 | Glassman |
| 5,345,946 A | 9/1994 | Butterworth |
| 5,380,278 A | 1/1995 | Mombrinie |
| 5,464,024 A | 11/1995 | Mills |
| D373,921 S | 9/1996 | Palomo |
| 5,778,889 A | 7/1998 | Jascomb |
| 5,778,890 A | 7/1998 | Lofgren |
| 5,800,483 A | 9/1998 | Vought |
| 5,803,086 A * | 9/1998 | Scholz ............... A61B 46/00 128/849 |
| 5,860,420 A | 1/1999 | Wiedner |
| 5,875,780 A | 3/1999 | Rodriguez |
| D408,533 S | 4/1999 | Niedospial, Jr. |
| 5,985,395 A * | 11/1999 | Comstock ............ A61B 46/00 128/855 |
| 5,991,666 A | 11/1999 | Vought |
| 6,007,564 A | 12/1999 | Haverstock |
| 6,019,102 A | 2/2000 | Becker |
| 6,032,670 A | 3/2000 | Miller |
| 6,199,553 B1 | 3/2001 | Hafer |
| 6,213,124 B1 | 4/2001 | Butterworth |
| 6,314,958 B1 | 11/2001 | Harroll |
| 6,345,621 B1 | 2/2002 | Chandler |
| D467,345 S | 12/2002 | Gingles |
| 6,497,233 B1 | 12/2002 | DeAngelis |
| 6,612,310 B2 | 9/2003 | Sklar |
| 6,694,981 B2 | 2/2004 | Gingles |
| 6,725,864 B2 | 4/2004 | Ewonce |
| 6,835,256 B2 | 12/2004 | Menzies |
| 6,843,252 B2 | 1/2005 | Harrison |
| 6,923,186 B2 | 8/2005 | Gavette |
| 6,966,320 B1 | 11/2005 | Baynes |
| 7,044,132 B2 | 5/2006 | Masini |
| 7,059,371 B2 | 6/2006 | Renn |
| 7,086,404 B2 | 8/2006 | Dusenbery |
| D539,904 S | 4/2007 | Inoue |
| D541,414 S | 4/2007 | Wallace |
| 7,588,034 B2 | 9/2009 | Mathis |
| D615,646 S | 5/2010 | Russell |
| 7,752,768 B2 | 7/2010 | Young |
| 7,853,311 B1 | 12/2010 | Webb |
| D637,296 S | 5/2011 | Matthews |
| 8,011,371 B2 | 9/2011 | Rotolo |
| 8,079,365 B2 | 12/2011 | Block |
| D653,330 S | 1/2012 | Ecabert |
| D653,331 S | 1/2012 | Ecabert |
| D653,333 S | 1/2012 | Ecabert |
| D653,751 S | 2/2012 | Ecabert |
| D653,752 S | 2/2012 | Pittet |
| D653,753 S | 2/2012 | Ecabert |
| 8,459,265 B2 | 6/2013 | Young |
| D693,603 S | 11/2013 | Esquivel |
| 8,721,629 B2 | 5/2014 | Hardman |
| 8,783,262 B2 | 7/2014 | Carrez |
| 8,967,150 B2 | 3/2015 | Carrez |
| D739,012 S | 9/2015 | Hanuka |
| 9,278,166 B2 | 3/2016 | Czajka, Jr. |
| D796,685 S | 9/2017 | Ohizep |
| D838,375 S | 1/2019 | Cashin |
| D839,440 S | 1/2019 | Cashin |
| 10,188,474 B2 | 1/2019 | Jarrelle |
| D851,772 S | 6/2019 | Haines |
| 2001/0023697 A1 | 9/2001 | Hinley |
| 2002/0174870 A1 | 11/2002 | Ewonce |
| 2003/0051362 A1 | 3/2003 | Buckman |
| 2003/0159966 A1 | 8/2003 | McMichael |
| 2003/0187458 A1 | 10/2003 | Carlson |
| 2003/0205233 A1 | 11/2003 | Aboul-Hosn et al. |
| 2004/0103903 A1 | 6/2004 | Falahee |
| 2004/0118049 A1 | 6/2004 | Chen |
| 2004/0118409 A1 | 6/2004 | Griesbach |
| 2005/0234322 A1 | 10/2005 | Lober |
| 2006/0169290 A1 | 8/2006 | Harris |
| 2006/0201521 A1 | 9/2006 | Masini |
| 2006/0207609 A1 | 9/2006 | Gil |
| 2006/0219249 A1 | 10/2006 | Czajka |
| 2008/0006279 A1 | 1/2008 | Bodenham |
| 2009/0158487 A1 | 6/2009 | Paulsen |
| 2009/0277460 A1 | 11/2009 | Carrez |
| 2010/0192960 A1 * | 8/2010 | Rotolo ............... A61B 46/00 128/854 |
| 2010/0263678 A1 | 10/2010 | Baumann |
| 2011/0015557 A1 | 1/2011 | Aali |
| 2011/0030702 A1 | 2/2011 | Czajka, Jr. |
| 2011/0041995 A1 * | 2/2011 | Adams ............... A61B 46/13 156/250 |
| 2011/0126845 A1 | 6/2011 | Hoffmann |
| 2011/0214679 A1 | 9/2011 | Chua |
| 2011/0247634 A1 | 10/2011 | Young |
| 2012/0017921 A1 | 1/2012 | Esquivel |
| 2012/0222686 A1 | 9/2012 | Lockwood |
| 2012/0222687 A1 | 9/2012 | Czajka |
| 2012/0298115 A1 | 11/2012 | Haines |
| 2013/0284187 A1 | 10/2013 | Esquivel |
| 2013/0304080 A1 | 11/2013 | Landry |
| 2013/0312770 A1 * | 11/2013 | Young ............... A61B 46/00 128/853 |
| 2014/0012119 A1 | 1/2014 | Geaghan |
| 2014/0261457 A1 | 9/2014 | Lother |
| 2015/0135398 A1 | 5/2015 | Czajka |
| 2015/0359596 A1 | 12/2015 | Jarrelle |
| 2016/0135915 A1 | 5/2016 | Czajka, Jr. |
| 2017/0258543 A1 | 9/2017 | Chua |

FOREIGN PATENT DOCUMENTS

| | | |
|---|---|---|
| CN | 101496742 | 3/2011 |
| CN | 102470019 | 5/2012 |

(56) References Cited

FOREIGN PATENT DOCUMENTS

| EP | 2151211 | 2/2010 |
|---|---|---|
| SU | 445412 | 10/1974 |
| WO | 9510986 | 4/1995 |
| WO | 2006094062 | 9/2006 |
| WO | 2011088326 | 7/2011 |
| WO | 2012078620 | 6/2012 |
| WO | 2012161869 | 11/2012 |
| WO | 2013036387 | 3/2013 |
| WO | 2014083573 | 6/2014 |
| WO | 2015191953 | 12/2015 |

OTHER PUBLICATIONS

Canadian Patent Application No. 2,832,104; Office Action dated Aug. 12, 2015; 5 pages.
Extended European Search Report from European Application No. 12751757.1 dated Aug. 12, 2014.
International Search Report and Written Opinion; PCT Patent Application No. PCT/US2014/023215; dated Jul. 24, 2014.
Notification of the First Office Action dated Mar. 20, 2015 from Chinese Patent Application No. 2012800215110.
PCT, Notification Concerning Transmittal of International Preliminary Report on Patentability, in International Application No. PCT/US2012/27284, dated Sep. 12, 2013.
PCT, Notification of Transmittal of the International Search Report and the Written Opinion of the International Searching Authority, or the Declaration, in International Application No. PCT/US12/27284, dated Jun. 29, 2012.
Chinese Patent Application No. 2012800215110; Office Action dated Nov. 4, 2015 with English translation.
Chinese Patent Application No. 2012800215110; Office Action dated Mar. 20, 2015 with English translation.
Australian Patent Application No. 2012223335; Patent Examination Report No. 2; dated Aug. 15, 2016; 6 pages.
Article 94(3) EPC from European Patent Application No. 12751757.1 dated Jan. 5, 2017; 7 pages.
International Search Report and Written Opinion from PCT/US2017/022278 dated Jun. 19, 2017; 11 pages.
International Search Report and Written Opinion from PCT/US2017/022450 dated Jun. 7, 2017; 12 pages.
Extended European Search Report from European Patent Application No. 17173255.5 dated Aug. 18, 2017; 10 pages.
European Extended Search Report for European Application No. 18200143 dated Mar. 29, 2019.
Medline Cesarean Section Surgical Drape with Pouch and Fenestration. No date specified. https://www.medline.com/product/Cesarean-Section-Surgical-Drape-with-Pouch-and-Fenestration/Z05-PF07160 (Year: 0).
European Supplementary Search Report for European Application No. 17767321, dated Oct. 18, 2019.
Australian Patent Application No. 2019200113; Patent Examination Report No. 1; dated May 10, 2019; 6 pages.
Chinese Office Action from corresponding Chinese Patent Application No. 201780017592.X dated Jul. 8, 2020 with English Translation; 22 pages.
Chinese Office Action with English translation from corresponding Chinese Patent Application No. 201780017592.X dated Jan. 27, 2021; 25 pages.

* cited by examiner

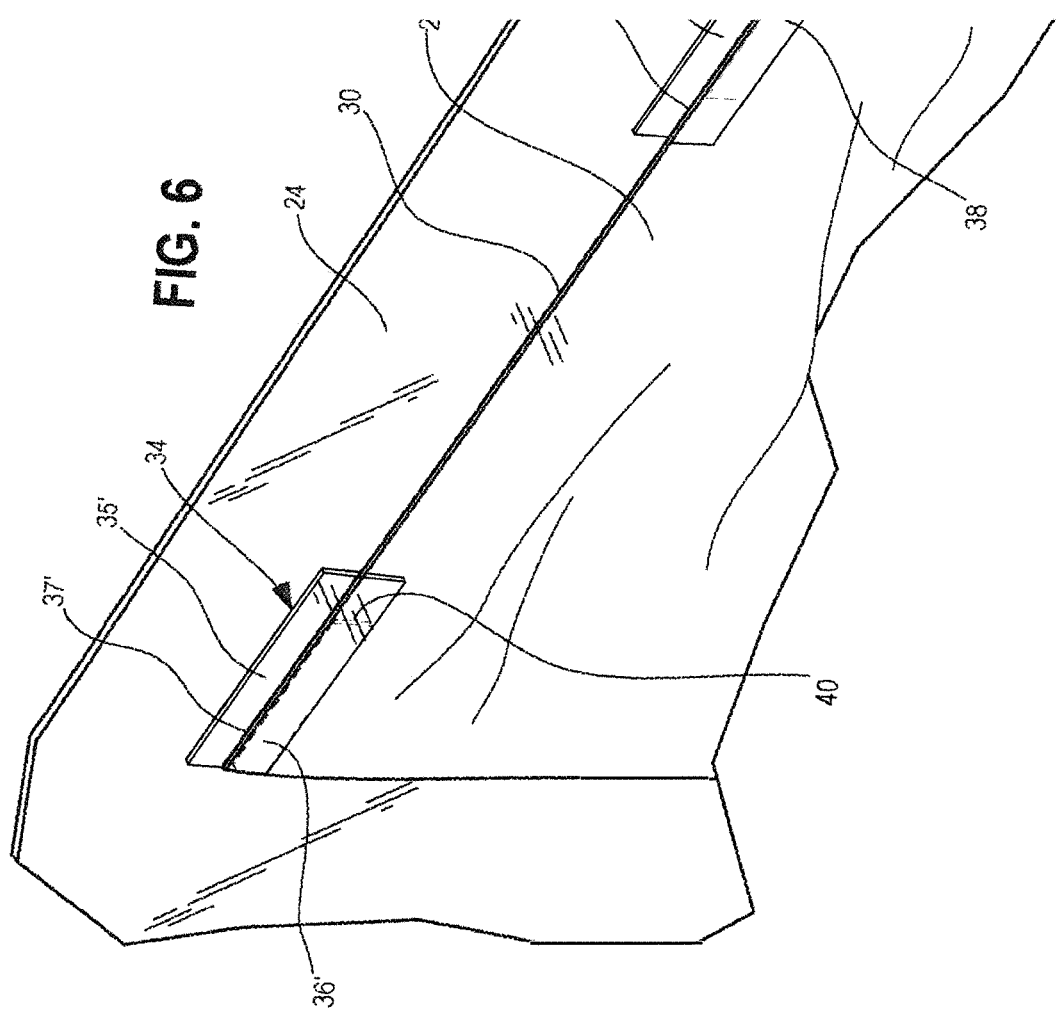

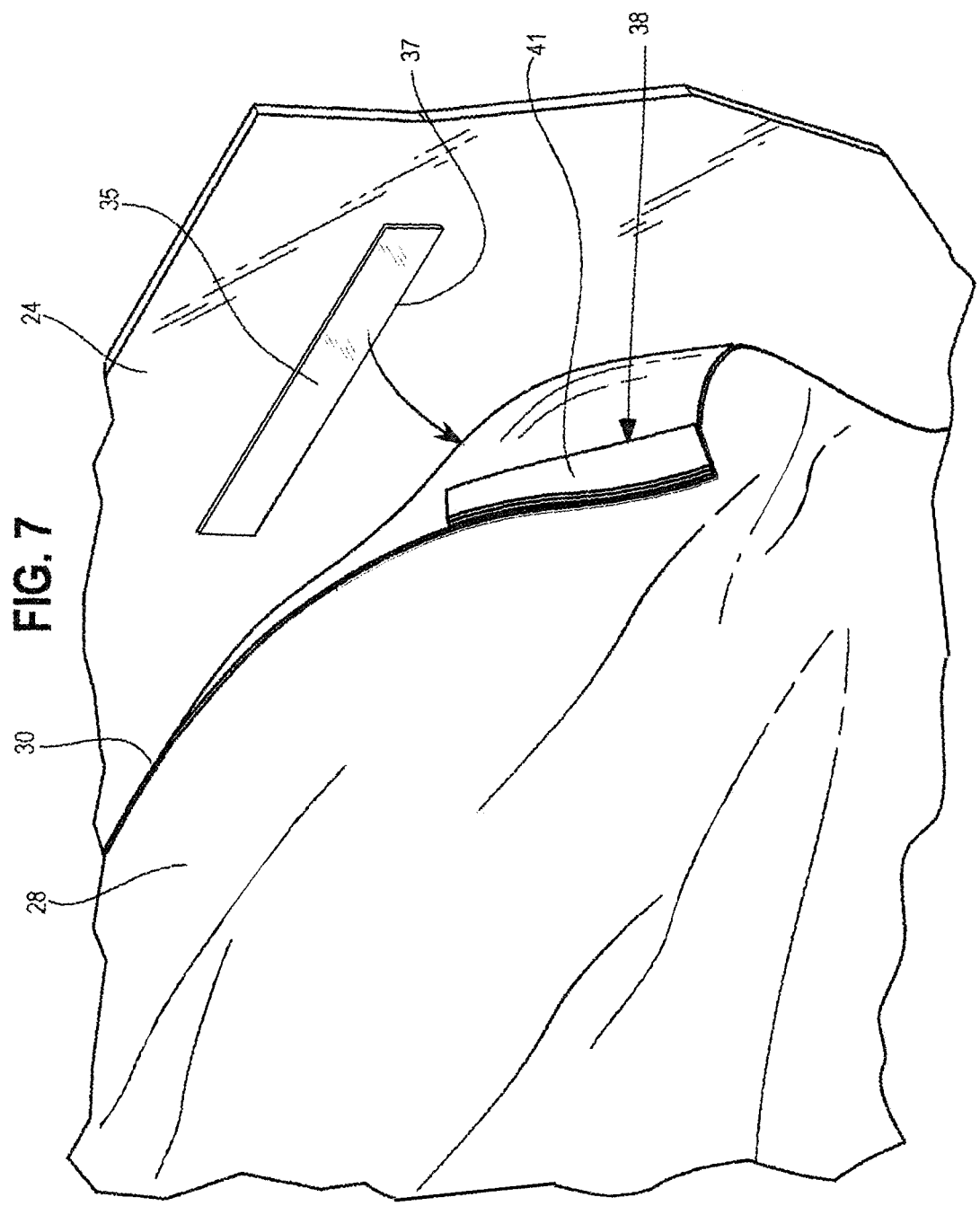

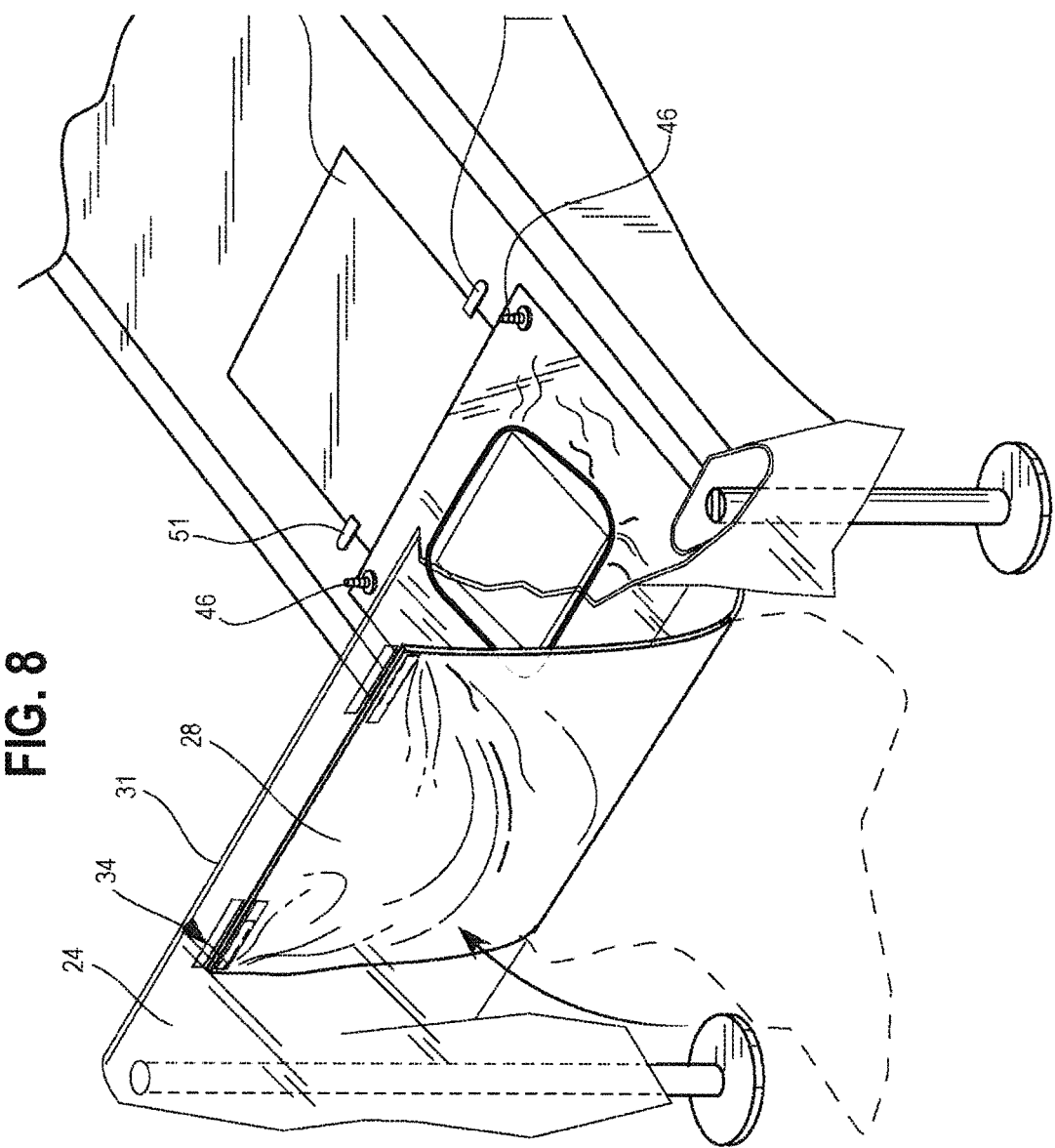

SURGICAL DRAPE

TECHNICAL FIELD

This patent relates to a drape for covering a patient during a surgical procedure.

BACKGROUND

Currently, a traditional Cesarean section procedure, also known as "C-section," is most commonly performed with the patient covered by a solid surgical drape. The drape is typically constructed of a multi-layer combination of spunbond and meltblown materials, commonly referred to as SMS nonwoven fabric.

Because the mother is typically awake and alert during the C-section, it is desirable to provide a barrier or screen to occlude the mother's view of the surgical area during the procedure. Many traditional drapes are in a "T" shape, with the top portion of the "T" acting as the anesthesia screen that obscures the patient's view of the surgical area. The drape is placed over the patient to isolate a sterile field near the patient's abdomen. The anesthesia screen is propped up on vertical standards at each side of the operating table near the patient's head or on a crossbar proximal the head.

In this arrangement, the mother does not have an opportunity to see her newborn immediately after delivery. It is desirable in the first moments after birth for the mother and child to establish an immediate connection. Because traditional surgical drapes obscure the mother's view of the newborn in the first moments after delivery, the mother and child do not have an opportunity to establish this immediate connection.

To address this concern, it is known to provide surgical drapes that incorporate a coverable window and an opaque flap that can be attached and detached to alternately obscure and expose the window. It has now been realized that many such known drapes are undesirable in that they are configured in ways that might allow for contamination of the surgical field once the flap is removed, particularly if the flap is folded into the surgical field.

A new surgical drape has now been devised. Generally, the drape includes a main sheet having a first patient-facing side and a second surgeon-facing side. The main sheet includes a fenestration through which a surgical procedure may be performed. The main sheet has a head region that is located near the head of the patient during the surgical procedure, and a substantially transparent sheet attached to the main sheet proximal the head region. The substantially transparent sheet allows the patient visual access to the surgeon-facing side from behind the substantially transparent sheet. The drape also includes also a substantially opaque screen attached to the patient-facing side of the substantially transparent sheet. This substantially opaque screen occludes the patient's visual access through the substantially transparent sheet when the substantially opaque screen is attached to the substantially transparent sheet. The substantially opaque screen is at least partially removable from the substantially transparent sheet to permit the patient viewing access through the substantially transparent sheet towards the area of the surgery. In this manner, the patient may view the birth of the infant or may view the infant immediately after birth.

The drape is configured such that the substantially opaque screen may be reattached to the patient side of the substantially transparent sheet to again occlude the patient's view of the surgical site. In this manner, the surgeon, after having permitted the patient to view the surgical site through the substantially transparent sheet, may occlude the patient's view of the surgical site so that, if desired, the surgeon can continue with the procedure with the surgical area again being occluded.

BRIEF DESCRIPTION OF THE DRAWINGS

FIG. 6 is a rear perspective view of an upper portion of the surgical drape as shown in FIGS. 1 and 4, enlarged with respect to FIGS. 1 and 4, and depicting a strip of material that connects the substantially opaque screen and the substantially transparent sheet.

FIG. 7 is a view similar to FIG. 6 but depicting the substantially opaque screen being removed from the substantially transparent sheet.

FIG. 8 is a view similar to FIG. 5 but with the substantially opaque screen reattached to the substantially transparent sheet.

Reference herein to "top" and bottom" are intended to relate the various views to one another and such reference is not intended to limit the orientation of the drape when in use.

DETAILED DESCRIPTION

Figure 1:
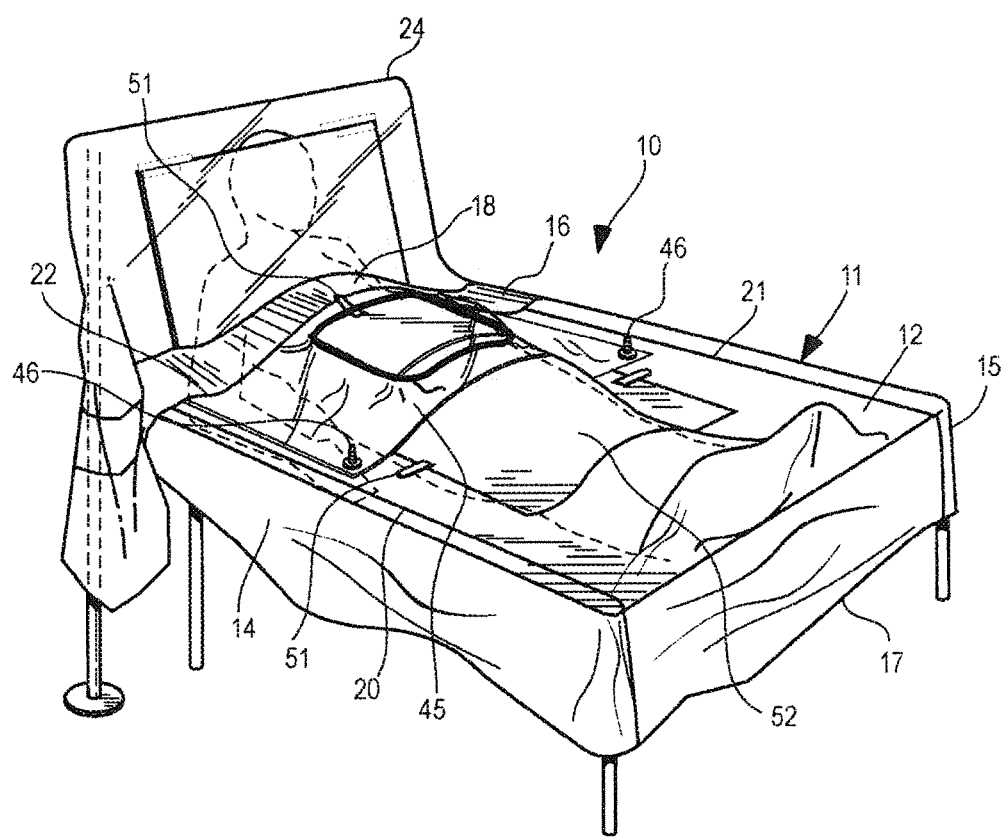
FIG. 1 is a perspective view of a surgical drape in accordance with one embodiment of the invention, shown in use positioned over a patient in a surgical bed.

Referring to FIG. 1, the surgical drape 10 includes a main sheet 11 having a center portion 12, first side portion 14, second side portion 15, and transverse portion 16. The center portion 12 has a bottom edge 17, a top edge 18, and first and second side edges 20 and 21 joining the bottom edge 17 and the top edge 18. The transverse portion 16 is attached to the center portion 12 near the top edge 18 of the center portion 12. The first side portion 14 is attached along the first side edge 20 of the center portion 12. The first side portion 14 is also attached along a lower edge 22 of the transverse portion 16. Similarly, the second side portion 15 is attached along the second side edge 21 of the center portion 12. The second side portion 15 is attached along the lower edge 22 of transverse portion 16.

The main sheet 11 and the transverse portion 16 may be constructed of any suitable material, and as shown are constructed of a multi-layer combination of spunbond and meltblown materials, commonly referred to as SMS nonwoven fabric. This combination provides a durable and absorbent flexible fluid barrier between the patient and the sterile field that are soft to the touch. The first and second side portions 14 and 15 are made of a flexible fluid impervious and non-absorbent material, such as polyethylene film.

Figure 2:
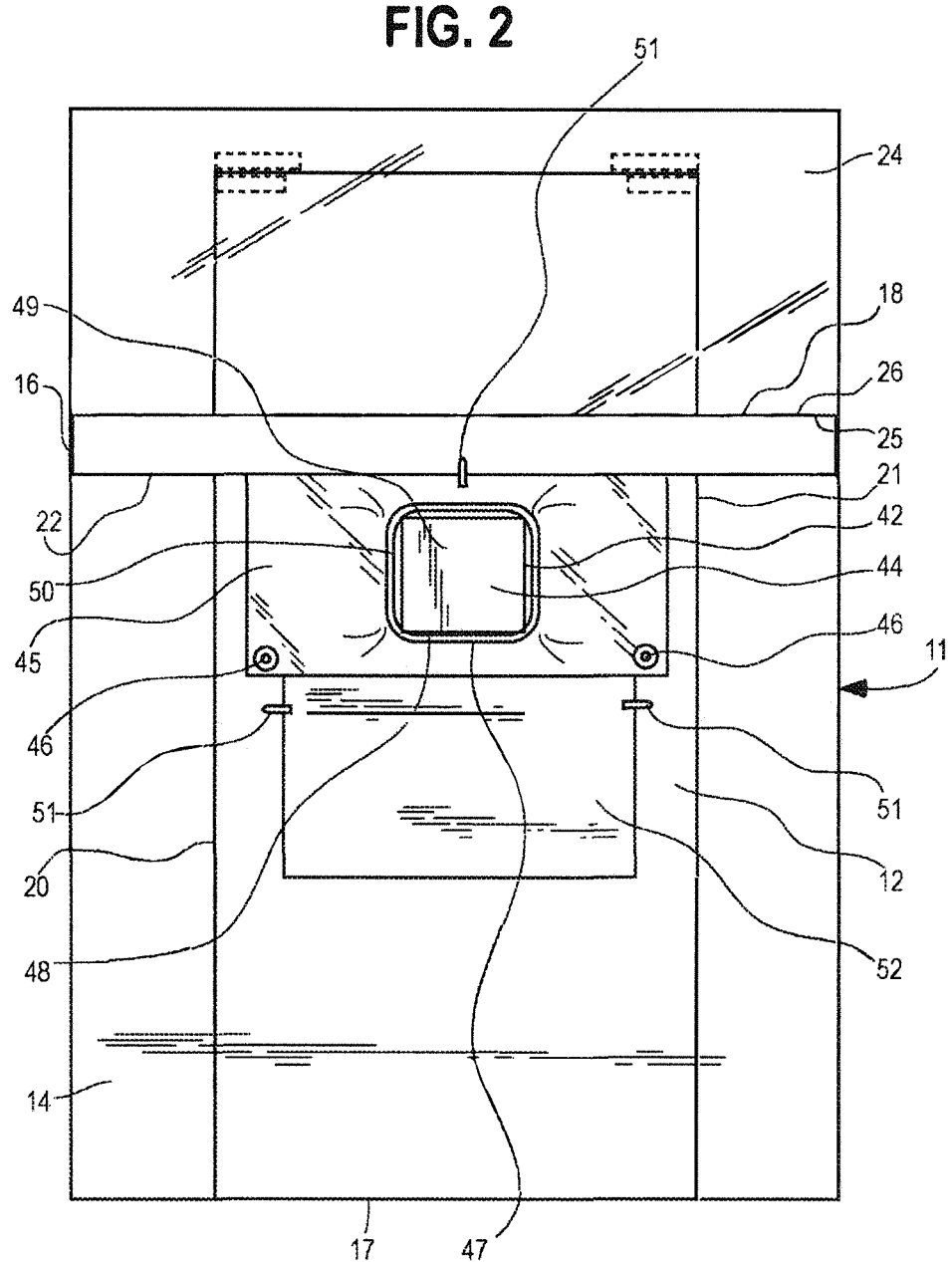
FIG. 2 is a top plan view of the surgical drape shown in FIG. 1.
Figure 3:
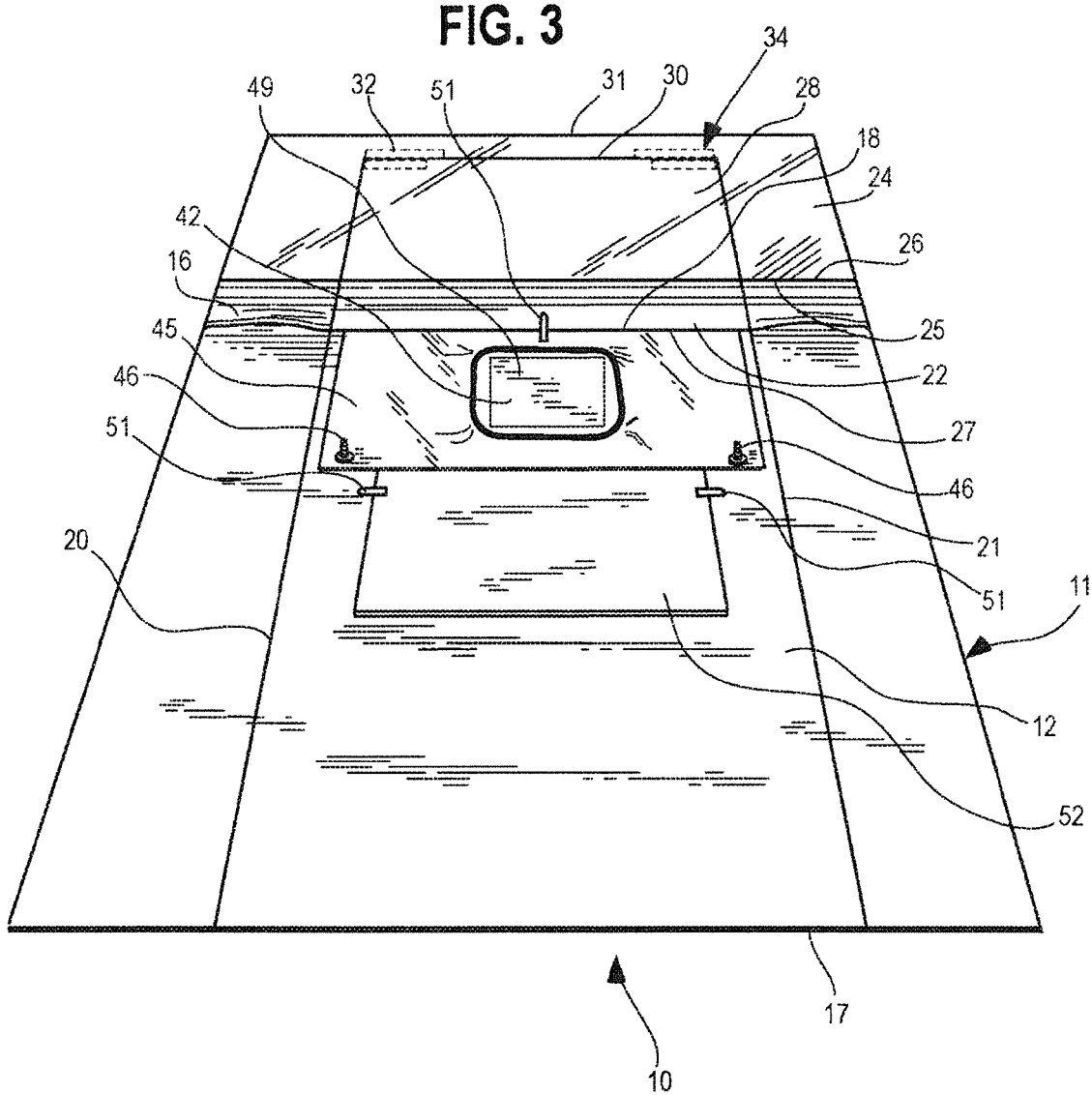
FIG. 3 is a front perspective view of the surgical drape shown in FIG. 1.

Referring to FIGS. 2 and 3, the surgical drape 10 also includes a substantially transparent sheet 24. A bottom edge 25 of the substantially transparent sheet 24 is attached along a top edge 26 of the transverse portion 16. The length of transverse portion 16 extends the width of the surgical drape 10. The substantially transparent sheet 24 may be made of any suitable material, such as polyethylene film. Further, as seen, the substantially transparent sheet extends across the entire surgical drape transverse width of the surgical drape.

The main sheet 11 includes a fenestration 42 through which a surgery accessing a patient's body may be performed. The fenestration 42 is an opening formed in the material of main sheet 11 sized according to the particular procedure for which the surgical drape 10 is to be used. In one embodiment, fenestration 42 is sized to allow sufficient access to a patient's abdominal region to perform a C-section procedure. Fenestration 42 is covered with a flexible adhesive film 44 known in the industry as "incise film," which may be formed from polyurethane or another suitable material to form a "full incise" fenestration. When the surgical drape 10 is laid over a patient, the flexible adhesive film 44 is first covered with a removable backing 49. Before the procedure is performed and after the surgical drape 10 is laid over the patient, the removable backing is removed from the flexible adhesive film 44, exposing the adhesive bottom surface of the flexible adhesive film 44. The flexible adhesive film 44 adheres to the skin of the patient. When the procedure is performed, incisions may be made directly through the flexible adhesive film 44.

As illustrated, flexible adhesive film 44 is a full panel film that covers the entirety of fenestration 42. It is contemplated that a "fenestrated incise" structure (not shown) alternatively may be employed, wherein there is adhesive disposed around the perimeter of the fenestration. This leaves an opening in a center portion of the flexible adhesive film through which the patient's skin is exposed to permit incisions to be made directly though the exposed skin.

With further reference to FIG. 2, the fenestration 42 may be substantially surrounded by a fluid collection pouch 45. The fluid collection pouch 45 is made of a plastic material impervious to fluid. The fluid collection pouch 45 surrounds the fenestration 42 in a sealing fashion such that any fluids released from the surgical site during the procedure will run off the sheet into fluid collection pouch 45. This prevents fluids from running off the main sheet 11 and onto the floor or other areas where fluids are not desired. The fluid collection pouch 45 may include one or more suction ports 46 for connection to suction equipment for aspirating the fluids from the fluid collection pouch.

The fluid collection pouch 45 includes an opening 47 through which the surgeon may access fenestration 42. The edges of the opening 48 may be bound by a formable material 50, such as a malleable wire encased in plastic. The formable material 50 allows the surgeon to shape the opening of fluid collection pouch 45 to allow for easier access to fenestration 42 or to reconfigure the shape of fluid collection pouch 45 in a manner that is most effective for the particular procedure.

The main sheet 11 includes one or more line anchors 51 for securing wires or lines to the surgical drape 10. The line anchors 51 consist of two plies of hook and loop material that may be separated at one end, but which are attached at another end. When the plies of the hook and loop material are separated, a line may be inserted between the two plies and when the plies are joined again, the hook and loop material captures the line between the two plies of material.

The main sheet 11 also includes an absorbent pad 52, which, as shown, is configured as a separate pad disposed on the main sheet 11. Absorbent pad 52 is located near fenestration 42 and is made up of a material suitable for absorbing fluids generated during the surgical procedure. The absorbent pad 52 provides another measure of fluid retention in the instance where fluids are not collected by the fluid collection pouch 45.

As supplied, the surgical drape 10 is initially provided in a sterile folded state wrapped in a sterile fabric wrapper (not shown) and an outer package (also not shown), as is conventional. The sterile fabric wrapper surrounds the surgical drape 10 to protect the surgical drape 10 and maintain its sterile state. The surgical drape 10 wrapped in the sterile fabric wrapper is enclosed in a plastic pouch. The plastic pouch further protects the surgical drape 10 and maintains its sterile condition.

Figure 4:
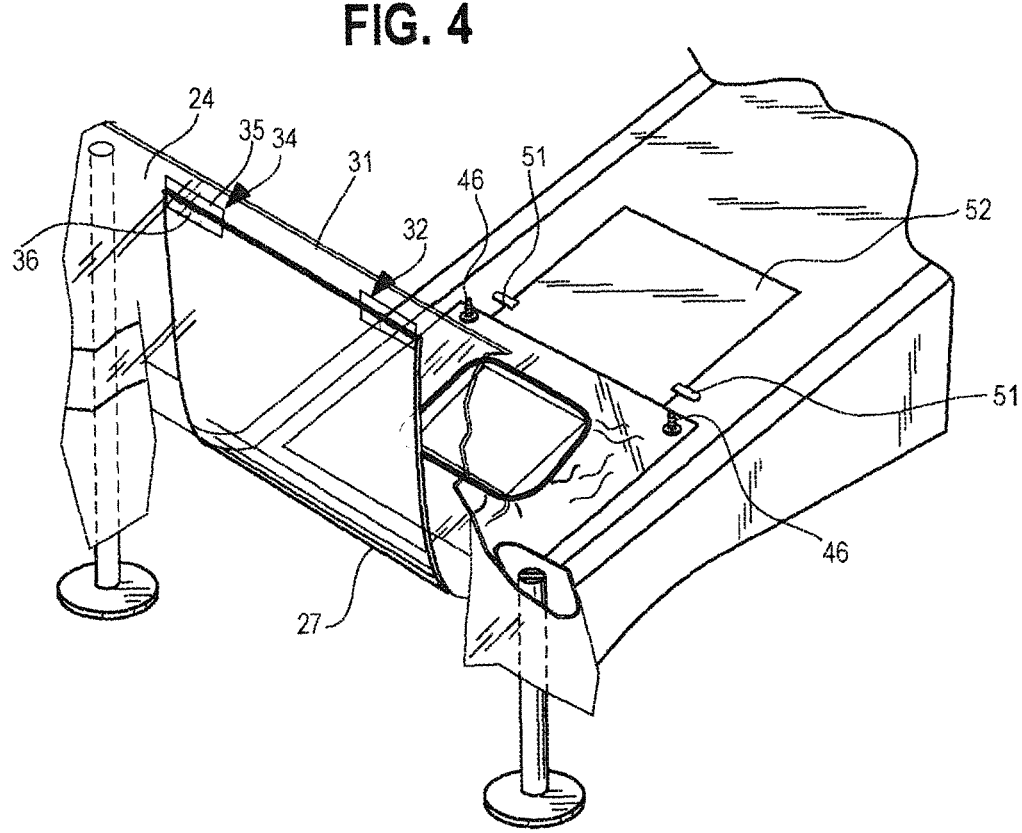
FIG. 4 is a rear perspective view, partially cut away, of the surgical drape and bed shown in FIG. 1, depicting the substantially opaque screen attached to the substantially transparent sheet.

Referring to FIGS. 3 and 4, a bottom edge 27 of a substantially opaque screen 28 is attached to the patient-facing side of the transverse portion 16 sufficiently to preclude the patient from viewing the surgical field beneath the screen. Preferably the screen is attached below the point at which the bottom edge 25 of the substantially transparent sheet 24 is attached to the top edge 26 of the transverse portion 16. The substantially opaque screen 28 may be made of any suitable material, such as SMS non-woven fabric. A top edge 30 of the substantially opaque screen 28 is attached proximate its outer edges to the patient-facing side of substantially opaque screen 28 proximal a top edge 31 of the substantially transparent sheet 28. The attachment is made via first and second adhesive tape strips 32 and 34 discussed in more detail below.

Referring to FIG. 6, the top edge 30 of the substantially opaque screen 28 is attached to the patent-facing side of the transparent sheet 24 via the first and second adhesive tape strips 32 and 34. First and second adhesive tape strips 32 and 34 include first regions, 35, 35' respectively, attached to the patient-facing side of the substantially transparent sheet 24. The strips include a second region 36, 36' respectively attached along the top edge 30 of the substantially opaque screen 28. The first and second regions of each adhesive tape strip are connected to one another along a demarcated line of weakness, such as strip scoreline 37, 37' that partially scores the first and second adhesive tape strips 32 and 34. The strip scorelines 37, 37' is generally formed by severing the first and second adhesive tape strips 32 and 34 along their lengths partially through their thickness such that a separated area is formed above the bridging area between the first region and the second region of each strip. In this embodiment, the strip scorelines 37, 37' are generally centrally positioned along the width of the first and second adhesive tape strips 32 and 34.

Figure 5:
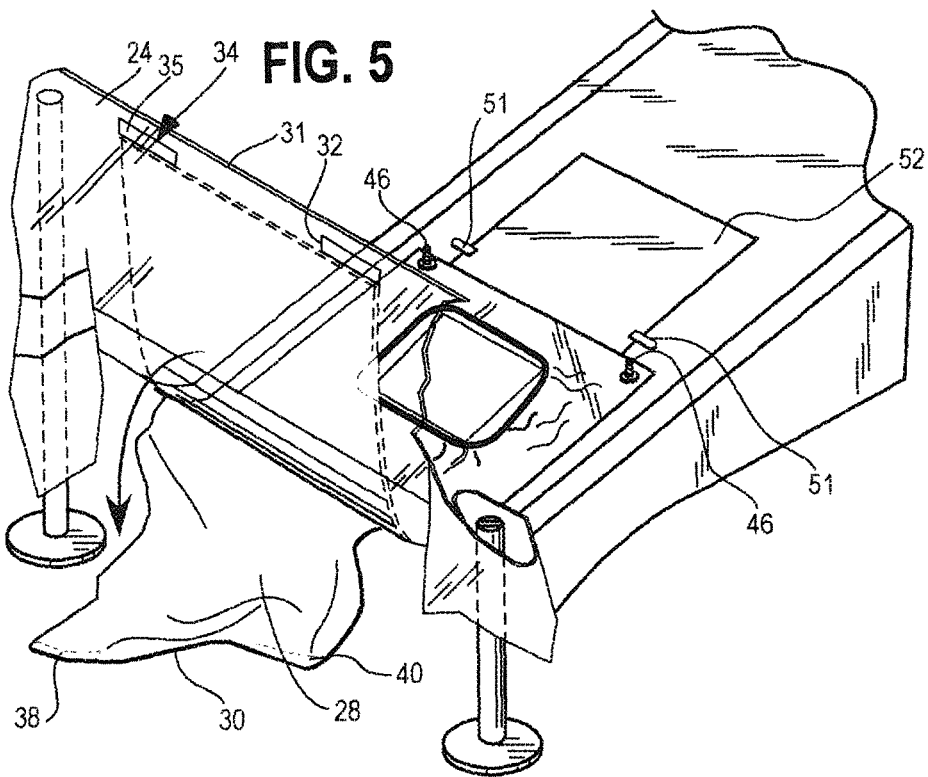
FIG. 5 is a view similar to FIG. 4 but depicting top edge of the substantially opaque screen having been separated from the substantially transparent sheet.

Thus, based at least in part on the relatively small thickness of the bridging area, the first region 35, 35' can be separated from the second region 36, 36' via manual tearing. Referring to FIG. 7, to detach the substantially transparent sheet 24 from the substantially opaque screen 28 a user may manually separate the first and second regions 35 and 36 of first and second adhesive tape strips 32 and 34. When the first and second regions 35 and 36 are severed along scoreline 37, the first region 35 remains attached to the patient-facing side of substantially transparent sheet 24. The second region 36 remains attached to the patient-facing side of substantially opaque screen 28. In this manner, the top edge 30 of the substantially opaque screen 28 is separated from the substantially transparent sheet 24. In this manner, the substantially opaque screen 28 may be detached and lowered to permit the patient to view the surgical area, as illustrated in FIG. 5.

Referring again to FIGS. 6 and 7, a first refastening strip 38 and a second refastening strip 40 are connected along the top edge 30 of the substantially opaque screen 28 on a side of the substantially opaque screen 28 proximal the first and second adhesive tape strips 32 and 34. First and second refastening strips 38 and 40 have two sides, both of which are covered by an adhesive. One side of each of the first and second refastening strips 38 and 40 is adhered to the substantially opaque screen 28. The other side of each of the refastening strips 38 and 40 is covered by a removable backing 41. The removable backing 41 may be removed to expose the adhesive material. Once the removable backing 41 is removed and the adhesive is exposed, the first and second refastening strips 38 and 40 may be used to re-adhere the substantially opaque screen 28 to the substantially transparent sheet 24 by pressing the exposed adhesive on refastening strips 38 and 40 to the patient-facing side of the substantially transparent sheet 24. Via these strips, after the patient views the surgical area, the substantially opaque screen 28 may be reattached to the substantially transparent sheet 24, as shown in FIG. 8.

As illustrated, the strips are disposed at the top of the screen, but other configurations are possible. For instance, the strips may be disposed at a different location on the screen, or may be provided on the substantially transparent sheet. Similarly, the sheet and screen are shown as being substantially rectilinear in configuration, but other shapes are possible, as is also possible for the main sheet. As an alternative to the adhesive strip, or in addition thereto, other implementations may be provided for refastening the substantially transparent sheet to the screen, these including, for instance, hook-and-loop material, ties, buttons, or other suitable fasteners. Such fasteners can be positioned in any manner suitable to effectuate refastening.

In using the surgical drape 10, the patient is first laid on a surgical table. Once the patient is in position on the surgical table, the surgical drape 10 is removed from the plastic pouch. At this point, the surgical drape 10 is enclosed within the sterile wrapper. A member of the surgical team may remove the wrapped surgical drape 10 from the container, and, by using methods known in the field, may unwrap the surgical drape 10 and present it to a member of the surgical team that has performed personal decontamination, such that the sterile state of the surgical drape 10 may be maintained during setup of the surgical procedure. After the surgical drape 10 is removed from the sterile wrapper, it is unfolded, and as it is unfolded it is lain over the patient. As it is unfolded and lain over the patient, when the portion of fenestration 42 is positioned over the surgical site of the patient, the removable adhesive backing is removed from the incise film 44, and the incise film 44 is adhered to the patient's skin and the site of the surgical area. The outer portions of substantially transparent sheet 24 are attached using spring clamps or other attaching means to N poles, or other standards used in operating rooms for positioning surgical drapes. The substantially transparent sheet 24 attached to the poles separates the patient's head from the sterile field. At this point in the procedure, the substantially opaque screen 28 remains attached to substantially transparent sheet 24 to occlude the view of the patient through the substantially transparent sheet 24, as seen in FIG. 4.

The surgical procedure may then proceed, and at a time at which the surgeon wishes to allow the patient to view an area around the surgical site, the substantially opaque screen 28 may be partially detached from substantially transparent sheet 24 to allow the patient to view the surgical area, as illustrated in FIG. 5. In the case of a C-section, this allows the new mother to view the newborn baby immediately after the baby is removed in the C-section procedure. After the mother has had an opportunity to view the baby, a member of the surgical team may reattach the substantially opaque screen 28 to the substantially transparent sheet 24 using the first and second refastening strips 38 and 40. The remainder of the surgical procedure may then be performed with the patient's vision in direction towards the surgical scene occluded.

It is thus seen that a drape that allows the surgeon to selectively permit the patient to view the area near the surgical field is provided. In a C-section procedure, the patient may or may not be able to view the actual surgical field, so long as she has a view through the substantially transparent sheet towards the surgeon-facing side of the drape. Notably, because the substantially opaque screen 28 remains outside of the sterile field, the risk of contamination is reduced even where the screen is removed and re-attached. The surgical drape 10 is particularly suitable for C-section procedures, but it is contemplated that the surgical drape 10 will find other surgical uses.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

The invention claimed is:

1. A surgical drape comprising:
   a mainsheet having a mainsheet transverse width at a head region for placement proximal a head of a patient during a surgical procedure, the mainsheet having a fenestration therein permitting access to a surgical region for performance of the surgical procedure when the drape covers the patient during the surgical procedure, and having a surgeon-facing side and a patient facing side;
   a substantially transparent sheet having a surgeon-facing side and a patient-facing side, the substantially transparent sheet having a transverse width substantially equal to the mainsheet transverse width and connected to the mainsheet at a connecting location, said connecting location being adjacent said head region and providing the patient with visual access therethrough; and a substantially rectilinear, substantially opaque screen attached to the patient-facing side of the substantially transparent sheet and effective to occlude the patient's visual access through the substantially transparent sheet at the substantially opaque screen, said substantially opaque screen covering a portion of the substantially transparent sheet, the portion of the substantially tranparent sheet being less than a total surface area of the substantially transparent sheet, the substantially opaque screen attached below the connecting location, said substantially opaque screen being at least partially removable from said substantially transparent sheet to thereby permit the patient's visual access through the substantially transparent sheet, the substantially opaque screen having top and bottom boundaries, the substantially opaque screen being removably attached to the patient-facing side of the substantially transparent sheet proximal the top boundary of the substantially opaque screen, further comprising a fluid collection pouch at least partially surrounding said fenestration.

2. The surgical drape of claim 1, the head region defining a top edge of the mainsheet.

3. The surgical drape of claim 1, the substantially opaque screen being reconnectable to the patient-facing side of the substantially transparent sheet after the substantially opaque screen has been at least partially removed from said substantially transparent sheet wherein upon reconnection the substantially opaque screen is again effective to occlude the patient's visual access through the substantially transparent sheet.

4. The surgical drape of claim 3, the drape being provided with an adhesive strip, the adhesive strip being covered with a removable covering material, the adhesive strip permitting reconnection of the substantially opaque screen to the patient-facing side of the substantially transparent sheet upon removal of the removable covering material.

5. The surgical drape of claim 1, the drape comprising a strip of material connecting the substantially transparent sheet to the substantially opaque screen, the strip of material having a demarcated line of weakness connecting first and second regions of the strip of material, the first region of the strip of material connected to the substantially transparent sheet and the second region of the strip of material connected to the substantially opaque screen.

6. A method, comprising:
applying the surgical drape of claim 1 to a patient;
at least partially disconnecting a substantially opaque screen portion of the surgical drape to allow the patient visual access to an area proximal a surgical region through the substantially transparent sheet of the surgical drape; and
reconnecting the at least partially disconnected substantially opaque screen portion of the surgical drape to the patient-facing side of the substantially transparent sheet to occlude the patient's visual access to an area proximal a surgical region.

7. The method of claim 6, where the partially disconnected substantially opaque screen portion is reconnected to the patient-facing side of the substantially transparent sheet by an adhesive strip.

8. The method of claim 6, where the substantially opaque screen is disconnected from the substantially transparent sheet by severing a strip of material connecting the substantially transparent sheet to the substantially opaque screen along a demarcated line of weakness connecting first and second regions of the strip of material, the first region of the strip of material connected to the substantially transparent sheet and the second region of the strip of material connected to the substantially opaque screen.

9. The surgical drape of claim 4, the drape being provided with at least one adhesive tape strip, the tape strip having a first region and a second region connected to one another along a demarcated line of weakness.

10. A surgical drape comprising:
a mainsheet having a fenestration therein permitting access to a surgical region for performance of a surgical procedure when the drape covers a patient during the surgical procedure, the mainsheet having a head region for placement proximal the head of the patient during the surgical procedure and having a surgeon-facing side and a patient-facing side;
a substantially transparent sheet having a surgeon-facing side and a patient-facing side and joined to the mainsheet at said head region for providing the patient with visual access therethrough; and
a substantially opaque screen attached to the patient-facing side of the substantially transparent sheet and effective to occlude the patient's visual access through the substantially transparent sheet, said substantially opaque screen being at least partially removable from said substantially transparent sheet to thereby permit the patient's visual access through the substantially transparent sheet, wherein the substantially transparent sheet has a first total surface area and the substantially opaque screen has a second total surface area that is less than the first total surface area of the substantially transparent sheet.

11. The surgical drape of claim 10 wherein the mainsheet has a mainsheet transverse width at a terminal edge adjacent the head region, and wherein the substantially transparent sheet has a transverse width substantially equal to the mainsheet transverse width.

12. The surgical drape of claim 10 wherein the substantially opaque screen has a screen transverse width that is less than a transverse width of the substantially transparent sheet.

13. The surgical drape of claim 10 wherein the substantially opaque screen has a screen height that is less than a height of the substantially transparent sheet.

14. A surgical drape comprising:
a mainsheet having a mainsheet transverse width at a head region for placement proximal a head of a patient during a surgical procedure, the mainsheet having a fenestration therein permitting access to a surgical region for performance of the surgical procedure when the drape covers the patient during the surgical procedure, and having a surgeon-facing side and a patient-facing side;
a substantially transparent sheet having a surgeon-facing side and a patient-facing side and having a transverse width substantially equal to the mainsheet transverse width, the substantially transparent sheet connected to the mainsheet at said head region for providing the patient with visual access therethrough; and
a substantially opaque screen attached to the patient-facing side of the substantially transparent sheet and effective to occlude the patient's visual access through the substantially transparent sheet, said substantially opaque screen being at least partially removable from said substantially transparent sheet to thereby permit the patient's visual access through the substantially transparent sheet, wherein the substantially transparent sheet has a first total surface area and the substantially opaque screen has a second total surface area that is less than the first total surface area of the substantially transparent sheet.

15. The surgical drape of claim 14 wherein the substantially opaque screen has a screen transverse width that is less than a transverse width of the substantially transparent sheet.

16. The surgical drape of claim 14 wherein the substantially opaque screen has a screen height that is less than a height of the substantially transparent sheet.

\* \* \* \* \*